United States Patent [19]

Belt et al.

[11] Patent Number: 5,033,284

[45] Date of Patent: Jul. 23, 1991

[54] CALIBRATION METHOD FOR GAS OR VAPOR RELATIVE CONCENTRATION SENSOR

[75] Inventors: Pekka Belt, Oulu; Lars Stormbom, Vantaa, both of Finland

[73] Assignee: Vaisala OY, Helsinki, Finland

[21] Appl. No.: 430,621

[22] Filed: Nov. 1, 1989

[30] Foreign Application Priority Data

Nov. 2, 1988 [FI] Finland .................................. 885062

[51] Int. Cl.$^5$ ............................................. G01D 18/00
[52] U.S. Cl. ..................................... 73/1 G; 73/23.21; 364/571.03
[58] Field of Search ........................ 73/1 G, 23.21; 364/571.01–571.08

[56] References Cited

U.S. PATENT DOCUMENTS

| | | | |
|---|---|---|---|
| 1,758,494 | 5/1930 | Behr | 364/571.03 X |
| 3,973,848 | 8/1976 | Jowett et al. | 73/23.31 X |
| 4,117,815 | 10/1978 | Ikeura | 73/23.31 X |
| 4,468,948 | 9/1984 | Nakayama | 73/19.1 |
| 4,500,940 | 2/1985 | Kuisma | 73/336.5 X |
| 4,505,804 | 3/1985 | Mase et al. | 204/425 |
| 4,532,016 | 7/1985 | Chambaz | 204/38.3 |
| 4,847,783 | 7/1989 | Grace et al. | 73/23.2 X |

FOREIGN PATENT DOCUMENTS

| | | | |
|---|---|---|---|
| 3140875 | 4/1983 | Fed. Rep. of Germany | 364/571.04 |
| 65674 | 2/1984 | Finland . | |
| 824393 | 11/1988 | Finland . | |
| 212761 | 12/1984 | Japan | 73/23.21 |
| 928291 | 5/1982 | U.S.S.R. | 73/1 G |

Primary Examiner—Tom Noland

[57] ABSTRACT

This invention concerns a calibration method and compatible sensor construction for the determination of relative concentration of a gas or vapor. According to the method a sensor is brought to controlled conditions, in which at least one calibration point is determined, and then with the help of the calibration point measurement values the response of the sensor for the measured gas or vapor is computed. According to the invention, both the temperature of the sensor and the relative concentration of the desired gas or vapor is measured at the actual measurement site, and the temperature of the sensor is deviated from the ambient temperature so transiently that the partial pressure of the measured gas or vapor can be assumed to stay at least approximately constant at the measurement site, whereby the results of measurements performed at each deviated temperature level can be used for computing a correction factor for the calibration of the sensor. An improved measurement accuracy results from the uncomplicated calibration routine.

4 Claims, 1 Drawing Sheet

CALIBRATION METHOD FOR GAS OR VAPOR RELATIVE CONCENTRATION SENSOR

BACKGROUND OF THE INVENTION

1. Field of the Invention

The present invention relates to a calibration method for the measurement of relative concentration of gas or vapor.

The invention also concerns a sensor construction applicable for the implementation of the method.

2. Description of Related Art

In this context, the relative concentration of gas or vapor is understood to refer to the ratio, which is the absolute concentration of the gas divided by the concentration of the gas at its saturation level. The relative concentration is conventionally used in, for instance, the determination of water vapor concentration (relative humidity).

The principal characteristics of measurement equipment are defined in terms of reliability and accuracy. For verification of these, different calibration methods are required.

An ideal solution for field calibration would be some form of automatic self-calibration. The implementation of this kind of self-calibration would be extremely difficult for most parameters.

Presently, most measurement instruments for relative concentration of gases and vapors are calibrated in controlled laboratory conditions.

A disadvantage of the prior art technology is that due to the awkward calibration routine, long calibration intervals are applied. Furthermore, this results in inaccurate measurements, because relative concentration meters are unstable by nature.

SUMMARY OF THE INVENTION

The present invention aims to overcome the disadvantages involved in the afore-described technology and to achieve an entirely novel calibration method for the measurement of relative concentration of gas or vapor.

The invention is based on measuring the temperature of the sensor element detecting the relative concentration of gas or vapor, while the temperature of the sensor element is deviated about the ambient temperature in order to establish unambiguous calibration points. This approach provides defined conditions of calibration for the measured parameter and/or deviates these conditions so as to obtain additional information on the measured parameter.

More specifically, the calibration method in accordance with the invention is such that at the actual measurement site, repetitive and at least approximately simultaneous measurements of both the temperature of the sensor and the relative concentration of the gas or vapor are performed, and the temperature of the sensor is deviated from the ambient temperature so rapidly that the partial pressure of the measured gas or vapor can be assumed to stay at least approximately constant at the measurement site, whereby the results of measurement used for computing a correction factor for the calibration of the sensor.

Furthermore, the sensor construction in accordance with the invention is such that a temperature sensor, placed to the immediate vicinity of the gas sensor for the measurement of the gas sensor temperature, and a temperature controlling device, placed to the vicinity of the gas sensor for the temperature control of gas sensor.

The invention provides outstanding benefits.

The invention facilitates automatic calibration in the concentration measurement of condensing gases (e.g., water vapor). The method also makes it possible to perform an accurate and quick calibration in field conditions without the removal of the gas sensor from the measured space. The shortened calibration intervals will essentially contribute to the measuring accuracy of the relatively unstable sensors used in the measurement of, e.g., relative humidity. An additional advantage is the appreciable lengthening of required service intervals.

The invention is next examined in detail with the help of the exemplifying embodiment illustrated in the attached drawing.

DETAILED DESCRIPTION OF PREFERRED EMBODIMENTS

The invention utilizes the fact that temperature is an easy parameter to measure and adjust even in field conditions and additionally the fact that the relative concentration of a condensing gas changes with temperature if the partial pressure of the gas is maintained constant.

A sensor sensitive to a condensing gas typically responds to the relative concentration of the measured gas, rather than to the absolute concentration. In this case the relative concentration of the measured gas can be defined as follows:

$$u = P_{gas}/P_s(T) \tag{1}$$

where
$P_{gas}$ = partial pressure of measured gas
$P_s(T)$ = partial pressure of measured gas at saturation (function of temperature)

If the response function of the sensor is of the type:

$$V = f(u) \tag{2}$$

then, the alteration of the sensor temperature (by heating or cooling) can be utilized to effect a change in the relative gas concentration detected by the sensor. For instance, the sensor can first be cooled down to the condensation temperature of the gas (making the activity to be a=1), and then heated sufficiently to achieve a very low activity (making a almost equal to 0). These two calibration points can then be utilized to perform a two-point calibration for the sensor. When required, several temperature levels can be used in calibration, whereby also the linearity of the sensor can also be measured.

Figure 1:
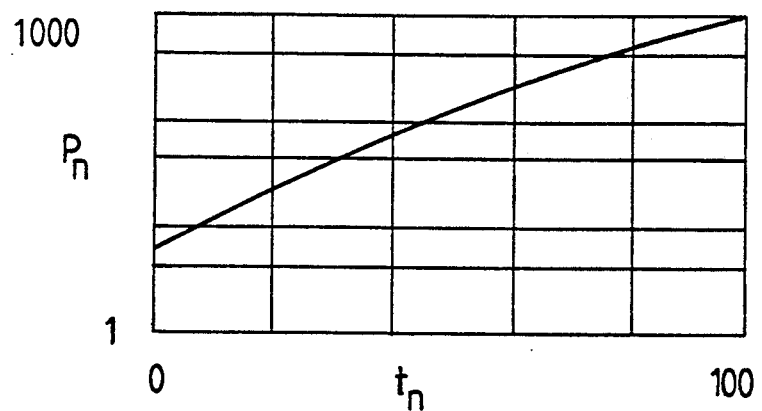
FIG. 1 shows in a graph the partial pressure of saturated water vapor as a function of temperature.

Shown in FIG. 1 is the partial pressure of saturated water vapor as a function of temperature.

As is evident from the diagram, the partial pressure of saturated gas is to a close approximation exponentially dependent on temperature.

In the exemplifying situation, ambient temperature is assumed to be 20° C. at a relative humidity of 50%

(equal to relative activity of 0.5). At these values, the actual partial pressure of water vapor is approximately 11.7 hPa. If, for instance, an offset-type measurement error of 5% is assumed, the reading of the measuring equipment would be 55% RH. Then, a partial pressure of water vapor computed from the reading and the ambient pressure would appear to be approximately 12.9 hPa. Next, the sensor of the measuring equipment will be heated to a temperature of, e.g., 100° C. causing the actual relative humidity imposed on the sensor to drop to 1.2%. With the assumption of the offset error in the sensor, the reading will then be 6.2%. Computation of relative humidity for the same situation on the basis of the first reading (55% RH, 20° C., computed partial pressure 12.9 hPa) results for the 100° C. temperature in 1.3% RH. On the basis of these two measurements, the self-calibrating apparatus is capable of performing a 4.9%-unit correction downward in its indication. The example case with heating the sensor to a temperature of 100° C. is to be considered only as one possible approach. An essential point is to heat the sensor sufficiently by at least, e.g., 60 K above the ambient temperature.

Described in the following is a calibration algorithm for a relative humidity sensor.

The presumption made is:

The sensor response can be described by the equations:

$$u = (C - C_0)/a \quad (3)$$

$$u = P_w/P_s(T)$$

where $P_w$ = partial pressure of water vapor $P_s(T)$ = partial pressure of saturated water vapor in temperature T 1. The sensor response is first measured in ambient temperature $T_1$:

$$C_1 = C_0 + a*P_w/P_s(T_1)$$

2. The sensor is then cooled so low as to attain the dewpoint in the determined manner and the response is measured:

$$C_2 = C_0 - a$$

3. The sensor is heated to a temperature $T_2$ above the ambient temperature and the response is measured:

$$C_3 = C_0 + a*P_w/P_s(T_2)$$

4. The prevailing partial pressure of water vapor can then be solved:

$$P_w = \frac{(C_1 - C_3)*P_s(T_1)}{C_2 - C_3 - P_s(T_1)/P_s(T_2)*(C_2 - C_1)} \quad (4)$$

5. The component $C_0$ can then be solved with the help of the prevailing partial pressure of water vapor:

$$C_0 = \frac{C_3 - C_2*P_w/P_s(T_2)}{1 - P_w/P_s(T_2)} \quad (5)$$

6. The sensor sensitivity a is solved:

$$a = C_2 - C_0 \quad (6)$$

In a similar manner the sensor behavior can be governed using another modelling function, e.g., a logarithmic or higher-order polynomial function, offering a better match with the sensor response.

If a more generalized approach is used by describing the sensor response as:

$$u(C) = \sum_{i=0}^{n} a_i * C^i \quad (7)$$

from which a set of n+1 measurements at different temperature levels will result in a set of n+1 equations:

$$P_s(T_s)\left(\sum_{i=0}^{n} a_i * C_s^i\right) - P_w = 0 \quad (8)$$

$$\sum_{i=0}^{n} a_i * C_{(n+1)}^i = 1 \quad (9)$$

This set of equation can then be solved for both the coefficients a and prevailing partial pressure $P_w$.

Figure 2:
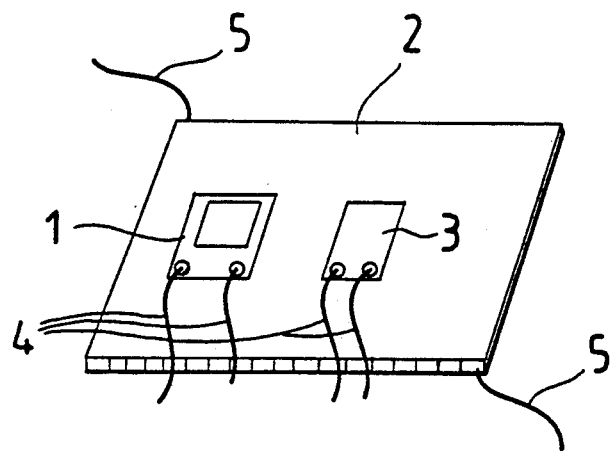
FIG. 2 shows a sensor construction compatible with the calibration method according to the invention.

Shown in FIG. 2 is a possible implementation of the heatable/coolable sensor construction.

The figure represents a gas sensor 1 and a temperature sensor 3, which both are bonded by, e.g., gluing to the flat surface of a Peltier element 2 comprised of bar-like elements alternating in a meandering way. The sensors 1 and 3 are further connected with conductors 4 to the electronics of the measurement circuitry. The Peltier element is correspondingly fed via conductors 5. An essential feature is to have the gas sensor 1 placed close to the temperature sensor 3 in order to obtain the highest possible accuracy in sensed temperature information. The gas sensor 1 can be of a type, for instance, called the Humicap sensor, which is described in, e.g., FI patent applications 824393 and 824392. Correspondingly, the temperature sensor 3 can be any type of commercially available temperature sensor, e.g., a solid-state semiconductor sensor or a resistive sensor. Typically, the temperature sensor used is a resistive platinum sensor. Connection of current to the Peltier element 2 allows the temperature of the sensors to be elevated or lowered according to the selected direction of current.

The calibration method is also applicable in the measurement of, e.g., alcohols or ammonia if the active sensor material in the first approximation of its response is dependent on the relative concentration of the gas, rather than being dependent on the absolute concentration.

What is claimed is:

1. A calibration method for the measurement of relative concentration of gas or vapor, comprising the steps of:

bringing a sensor to controlled conditions, in which at least one calibration point is determined; and computing the response of the sensor for the relative concentration of measured gas or vapor with the help of the determined calibration point, wherein at the actual measurement site, repetitive and at least approximately simultaneous measurements of both the temperature of the sensor and the relative concentration of the gas or vapor are performed, and the temperature of the sensor is deviated from the ambient temperature so rapidly that the partial pressure of the measured gas or vapor can be assumed to stay at least approximately constant at the measurement site, whereby the results of measurement performed at each deviated temperature level can be used for computing a correction factor for the calibration of the sensor.

2. A calibration method in accordance with claim 1, wherein for the determination of the calibration point of 100% relative concentration, the sensor is cooled down to such a low temperature that the gas or vapor will condense.

3. A calibration method in accordance with claim 1, wherein in order to establish a calibration point of low relative concentration, the sensor is heated by at least 60 K above the ambient.

4. A calibration method in accordance with claims 1, 2 or 3, wherein the temperature deviation of the sensor is implemented using a Peltier element.

* * * * *